US010575786B2

(12) United States Patent
Alam et al.

(10) Patent No.: US 10,575,786 B2
(45) Date of Patent: Mar. 3, 2020

(54) SYSTEM AND METHOD FOR PHOTOPLETHYSMOGRAM (PPG) SIGNAL QUALITY ASSESSMENT

(71) Applicant: Tata Consultancy Services Limited, Mumbai (IN)

(72) Inventors: Shahnawaz Alam, Kolkata (IN); Shreyasi Datta, Kolkata (IN); Anirban Dutta Choudhury, Kolkatta (IN); Arpan Pal, Kolkata (IN)

(73) Assignee: Tate Consultancy Services Limited, Mumbai (IN)

( * ) Notice: Subject to any disclaimer, the term of this patent is extended or adjusted under 35 U.S.C. 154(b) by 197 days.

(21) Appl. No.: 15/912,773

(22) Filed: Mar. 6, 2018

(65) Prior Publication Data

US 2019/0133533 A1 May 9, 2019

(30) Foreign Application Priority Data

Nov. 6, 2017 (IN) .............................. 201721039519

(51) Int. Cl.
*A61B 5/00* (2006.01)
*A61B 5/024* (2006.01)
(Continued)

(52) U.S. Cl.
CPC ........ *A61B 5/7221* (2013.01); *A61B 5/02416* (2013.01); *A61B 5/02438* (2013.01);
(Continued)

(58) Field of Classification Search
CPC .............. A61B 5/7221; A61B 5/02416; A61B 5/02438; A61B 5/14542; A61B 5/1422;
(Continued)

(56) References Cited

U.S. PATENT DOCUMENTS 9,179,876 B2 * 11/2015 Ochs ...................... A61B 5/743
2012/0075256 A1 3/2012 Izadi et al.
2016/0220188 A1 * 8/2016 Chon ................... A61B 5/1455

FOREIGN PATENT DOCUMENTS

WO WO 2017-089921 A1 6/2017

OTHER PUBLICATIONS

Christina Orphanidou, et al. "Signal-Quality Indices for the Electrocardiogram and Photoplethysmogram: Derivation and Applications to Wiresless Monitoring," IEEE Journal of Biomedical and Health Informatics, vol. 19, No. 3, pp. 832-838.

* cited by examiner

*Primary Examiner* — Lindsey G Wehrheim
(74) *Attorney, Agent, or Firm* — Finnegan, Henderson, Farabow, Garrett & Dunner LLP

(57) ABSTRACT

This disclosure relates generally to PPG signal quality assessment, and more particularly to, a system and method for sensor agnostic PPG signal quality assessment using morphological analysis. In one embodiment, a method for PPG signal quality assessment includes obtaining a PPG signal captured using a testing device in real-time, and segmenting into a first plurality of PPG signal samples such that length of each of the first plurality of PPG signal samples more than a threshold length. A signal sufficiency check (SSC) is performed for each first PPG signal sample to obtain at least a first set of PPG signal samples complying with the SSC. A set of features is extracted from the first set of PPG signal samples, based on which each PPG signal sample is identified as one of a noisy and clean signal sample using a plurality of Random Forest (RF) models created during the training phase.

15 Claims, 14 Drawing Sheets

(51) Int. Cl.
*A61B 5/145* (2006.01)
*A61B 5/1455* (2006.01)
(52) U.S. Cl.
CPC ........ *A61B 5/1455* (2013.01); *A61B 5/14542* (2013.01); *A61B 5/6898* (2013.01); *A61B 5/7203* (2013.01); *A61B 5/7246* (2013.01); *A61B 5/7267* (2013.01)
(58) Field of Classification Search
CPC ... A61B 5/6898; A61B 5/7203; A61B 5/7246; A61B 5/7267
See application file for complete search history.

PPG SIGNAL SAMPLE        TEMPLATE

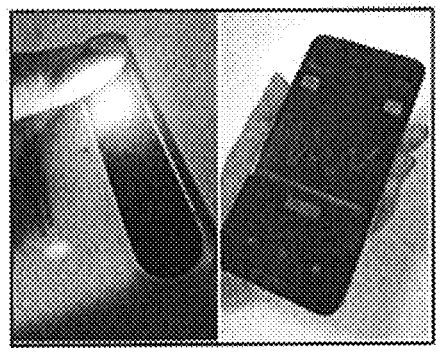 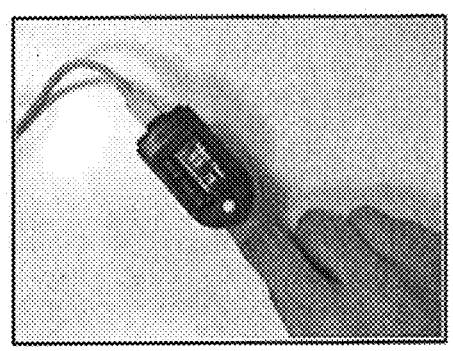
FIG. 10A  FIG. 10B
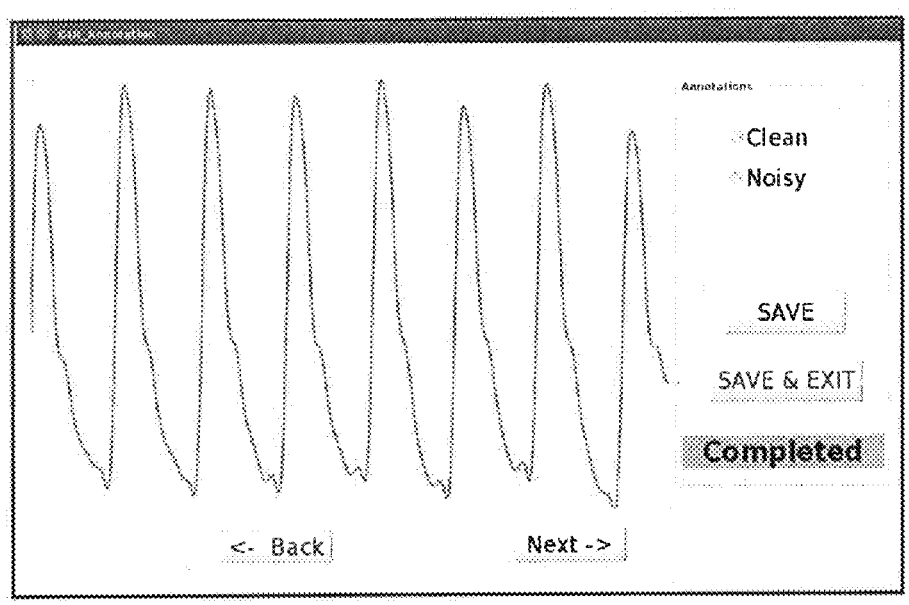
FIG. 11

SYSTEM AND METHOD FOR PHOTOPLETHYSMOGRAM (PPG) SIGNAL QUALITY ASSESSMENT

PRIORITY CLAIM

This U.S. patent application claims priority under 35 U.S.C. § 119 to: India Application No. 201721039519, filed on Nov. 6, 2017. The entire contents of the aforementioned application are incorporated herein by reference.

TECHNICAL FIELD

This disclosure relates generally to Photoplethysmogram (PPG) signal quality assessment, and more particularly to, a system and method for sensor agnostic PPG signal quality assessment using morphological analysis.

BACKGROUND

Photoplethysmogram (PPG) signal obtained at the fingertip indicates a volumetric fluctuation of blood in finger arterioles. The PPG waveform is periodic in nature and its fundamental frequency indicates the heart rate (HR). There has been a growth of development of technologies for real-time monitoring of vital signs using PPG signal captured using wearable devices, as PPG has important information which can be correlated to certain symptoms and diseases. However, PPG signals are prone to noise, due to motion artefacts, poor blood perfusion and changes in ambient light. These artefacts impede the usability of PPG signal in real-time assessment/monitoring applications like false alarms in an Intensive Care Unit (ICU), inaccuracy in vital measurements like blood pressure, screening of other diseases, and so on. Hence, it is important to check quality of continuous PPG signal before measuring vitals. Also, in home care or rural setup, where people are not trained to collect PPG data, a real-time feedback of signal quality can help to capture clean signal.

SUMMARY

Embodiments of the present disclosure present technological improvements as solutions to one or more of the above-mentioned technical problems recognized by the inventors in conventional systems. For example, in one embodiment, a processor-implemented method for PPG signal quality assessment is provided. The method includes obtaining a PPG signal captured using a testing device in real-time, via one or more hardware processors. Further the method includes segmenting, via the one or more hardware processors, the PPG signal into a first plurality of PPG signal samples, where length of each of the first plurality of PPG signal samples more than a threshold length. Furthermore, the method includes performing, via the one or more hardware processors, signal sufficiency check (SSC) for each first PPG signal sample of the first plurality of PPG signal samples to obtain at least a first set of PPG signal samples complying with the SSC. The SSC is performed to determine whether the first plurality of PPG signal samples comprises sufficient information for the real-time PPG signal quality assessment. Moreover, the method includes extracting a set of features from the first set of PPG signal samples, via the one or more hardware processors, the set of features representing an optimal set of features derived from a pre-stored training data by a training model during a training phase. Also, the method includes identifying, based on the set of features, each of the set of PPG signal samples as one of a noisy signal sample and a clean signal sample using a plurality of Random Forest (RF) models created during the training phase, via the one or more hardware processors.

In another embodiment, a system for PPG signal quality assessment is provided. The system includes one or more memories; and one or more hardware processors, the one or more memories coupled to the one or more hardware processors, wherein the at least one processor is capable of executing programmed instructions stored in the one or more memories to obtain a PPG signal captured using a testing device in real-time. Further one or more hardware processors are configured by the instructions to segment the PPG signal into a first plurality of PPG signal samples, where length of each of the first plurality of PPG signal samples more than a threshold length. Furthermore, the one or more hardware processors are further configured by the instructions to perform a signal sufficiency check (SSC) for each first PPG signal sample of the first plurality of PPG signal samples to obtain at least a first set of PPG signal samples complying with the SSC. The SSC is performed to determine whether the first plurality of PPG signal samples comprises sufficient information for the real-time PPG signal quality assessment. Moreover, the one or more hardware processors are further configured by the instructions to extract a set of features from the first set of PPG signal samples, the set of features representing an optimal set of features derived from a prestored training data by a training model during a training phase. Also, the one or more hardware processors are further configured by the instructions to identify, based on the set of features, each of the set of PPG signal samples as one of a noisy signal sample and a clean signal sample using a plurality of Random Forest (RF) models created during the training phase.

In yet another embodiment, a non-transitory computer-readable medium having embodied thereon a computer program for executing a method for PPG signal quality assessment is provided. The method includes obtaining a PPG signal captured using a testing device in real-time, via one or more hardware processors. Further the method includes segmenting the PPG signal into a first plurality of PPG signal samples, where length of each of the first plurality of PPG signal samples more than a threshold length. Furthermore, the method includes performing, signal sufficiency check (SSC) for each first PPG signal sample of the first plurality of PPG signal samples to obtain at least a first set of PPG signal samples complying with the SSC. The SSC is performed to determine whether the first plurality of PPG signal samples comprises sufficient information for the real-time PPG signal quality assessment. Moreover, the method includes extracting a set of features from the first set of PPG signal samples, the set of features representing an optimal set of features derived from a prestored training data by a training model during a training phase. Also, the method includes identifying, based on the set of features, each of the set of PPG signal samples as one of a noisy signal sample and a clean signal sample using a plurality of Random Forest (RF) models created during the training phase.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 10A and 10B illustrated example data collection scenarios for PPG signal quality assessment using Smartphone camera with flash light on, and Pulse Oximeter, respectively in accordance with some embodiments of the present disclosure FIG. 11 illustrates an example annotation GUI for PPG signal quality assessment in accordance with some embodiments of the present disclosure.

DETAILED DESCRIPTION

Figure 1:
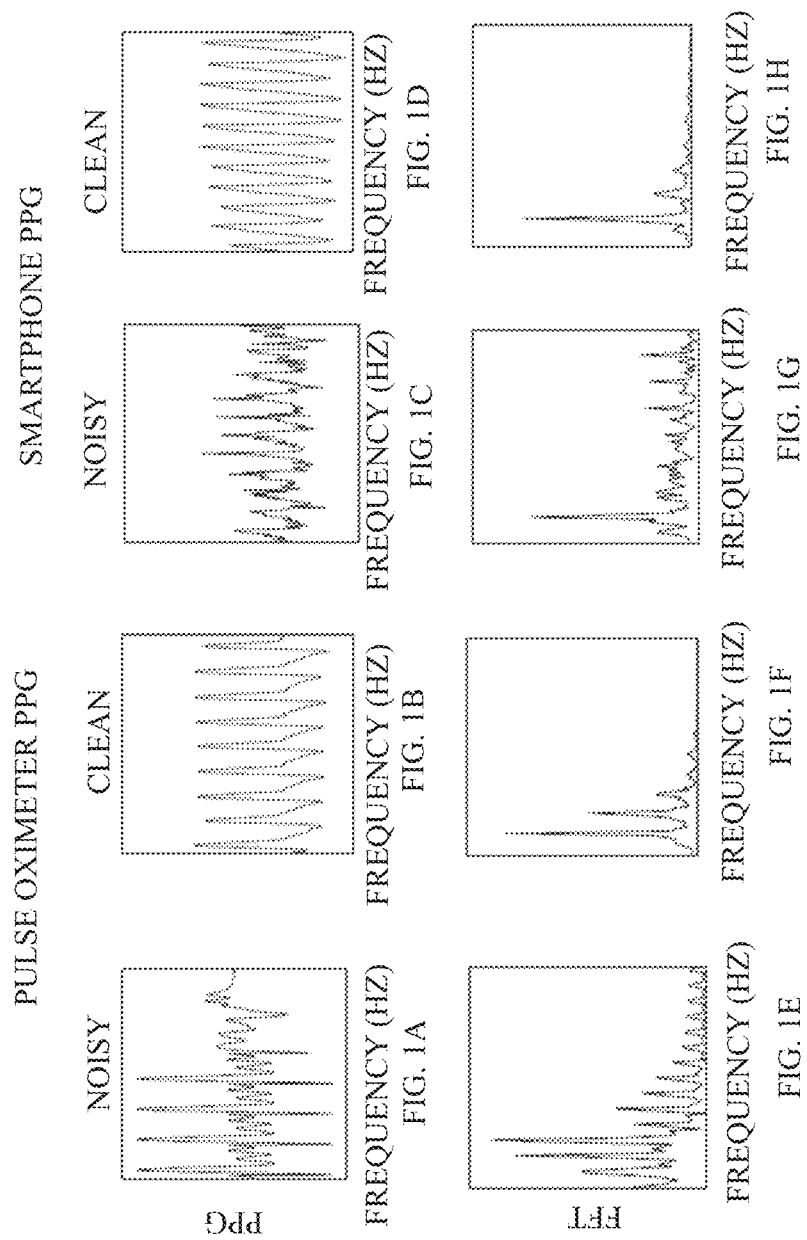
FIGS. 1A and 1B illustrate examples of clean and noisy PPG signals captured from a Pulse Oximeter according to some embodiments of the present disclosure.
FIGS. 1C and 1D illustrate examples of clean and noisy PPG signals from a Smartphone according to some embodiments of the present disclosure.
FIGS. 1E and 1F illustrate examples of clean and noisy FETs corresponding to the clean and noisy PPG signals of FIGS. 1A and 1B.
FIGS. 1G and 1H illustrate examples of clean and noisy FETs corresponding to the clean and noisy PPG signals of FIGS. 1C and 1D.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

There has been a growing interest in the real-time monitoring of vital signs using PPG signal captured using wearables, as PPG has important information which can be correlated to certain symptoms and diseases. However, PPG signals are prone to noise, due to motion artefacts, poor blood perfusion and changes in ambient light. These artefacts impede the usability of PPG signal in real-time assessment/monitoring applications.

Pulse oximeter, a mobile monitoring device is the ubiquitous non-invasive device to extract PPG signal used for measuring heart rate (HR) and oxygen saturation levels. However, recent increase in the use of smartphone and wearable devices with inbuilt camera and IR sensors has broadened the scope of sensor exploitation. These sensors may be employed for extraction of PPG for mobile healthcare solutions. However, the main challenge lies in the heterogeneity of these sensors. Particularly, smartphone cameras, when compared to pulse oximeter, are non-medical grade and have varied set of hardware specifications and efficiency, which impacts the PPG waveform vastly. Their low and vacillating sampling frequency (frames per second) and presence of inherently unstable reflective sensing (wherein transmitter and receiver are on the same side) degrades the accuracy of the captured PPG signal, resulting in the PPG samples obtained from smartphones being more prone to noise and artefacts than pulse oximeter counterpart, as shown in FIGS. 1A-1H.

Referring to FIGS. 1A-1H, clean and noisy PPG signal samples captured from Pulse Oximeter and smartphone with corresponding FFT are illustrated. For example, FIGS. 1A and 1B illustrates noisy and clean PPG signal samples, respectively collected from a pulse oximeter, and FIGS. 1E and 1F, respectively illustrates FFT signals corresponding to the PPG signal samples of FIGS. 1A and 1B, respectively. Similarly, FIGS. 1C and 1D illustrates noisy and clean PPG signal samples, respectively collected from a smartphone, and FIGS. 1G and 1H illustrates FFT signals corresponding to the PPG signal samples of FIGS. 1C and 1D, respectively.

As is seen from FIGS. 1A-1H, the accuracy of the PPG samples obtained from smartphones are more prone to noise and artefacts than those obtained from the pulse oximeter. Accordingly, a generalized PPG signal assessing technique, portable across devices may be suitable.

Various conventional techniques for PPG signal quality assessment are existing. For example, in one technique, a system is proposed where four Signal Quality Indices (SQIs), having thresholds set empirically through trial and error, are fused into one (termed as "qSQI") and used to classify each beat's quality in the dataset. Nevertheless, initial 30 seconds of every session are considered for online template creation that are not being employed for analysis, thus making the system infeasible to be implemented in real-time scenarios, where there is limited time for analysis and estimation. Another known technique includes two levels of hierarchical rule based classification to eliminate inadequate and fallacious samples. However, thresholds of the SQIs are not provided, and in addition, SQIs like pulse width and pulse amplitude threshold employed herein vary a lot depending upon the pressure exerted on the sensor, sample resolution of sensor and heart rate of subject; hence cannot be generalized.

Yet another known technique makes use of hierarchical rule engine to obviate bad PPG samples using rigorous constraints, wherein the sample is predicted "bad" on failure of even one criterion. Moreover, thresholds on template matching correlation SQI in this technique varies across devices, for example smartphone based PPG signal tends to have lower correlation coefficient than pulse oximeter counterpart due to low sampling rate and sensitivity of the camera sensor. Another known technique employs a statistical approach to find out the optimal SQI for assessing PPG samples, in which out of 8 SQIs stated, "skewness" index is said to outperform. But such indices are validated on a small number of PPG samples collected using the same sensor and hence are liable to fail across different types of sensors. Most of these techniques use heuristically determined thresholds to assess PPG signals which might limit their use to a specific device or system. Hence, a robust sensor agnostic PPG quality checker, focusing on stable PPG features that are sensor independent is desirable.

A signal with good signal quality refers to a signal whose morphological properties remain stable over time without having artefacts. Nevertheless, fluctuations of the signal due to variations in physiological vitals like Heart Rate (HR) or Blood Pressure (BP) might alter the signal morphology, but this should not perturb the decision of the noise detection algorithm. Thus, the system/technique should be sensitive only to artefacts, and not to the other variations in the PPG waveform, occurring due to pathological conditions.

Various embodiments disclosed herein describes system and method to detect PPG signals that are free from artefacts and can be used for clinical purposes, using an ensemble based classifier over novel PPG waveform based SQIs.

As is known by conventional techniques, PPG signal annotation is not a straightforward or simple process. In an existing annotation methodology based on Heart Rate (HRs), the annotation is a binary decision—"good" (i.e., having reliable HR) and—"bad". In other words, if a heartbeat derived from a PPG sample is found to be in a particular range, the sample is classified as clinically fit. This, however, may not only work in cases where the goal is to detect HR, but for evaluating complex physiological process it provides an incomplete view of the PPG signal. PPG waveform can be morphed easily due to it's sensitivity towards body motion and sensor error, wherein signal might alter with the introduction of non-stationary variation. Therefore, in such cases HR component might be visible in frequency domain, however, the component of artefacts may also be prominent as seen in FIGS. 1A-1H, including higher frequency noises. Therefore, to tackle aforementioned challenges, the disclosed embodiments address the waveform morphology to annotate the PPG signals, as will be described further in the description. A network implementation for PPG signal quality assessment in accordance with various embodiments of the present disclosure is presented here with reference to FIG. 2.

The methods and systems are not limited to the specific embodiments described herein. In addition, the method and system can be practiced independently and separately from other modules and methods described herein. Each device element/module and method can be used in combination with other elements/modules and other methods.

The manner, in which the system and method for PPG signal quality assessment shall be implemented, has been explained in details with respect to the FIGS. 2 through 19B. While aspects of described methods and systems for PPG signal quality assessment can be implemented in any number of different systems, utility environments, and/or configurations, the embodiments are described in the context of the following exemplary system(s).

Figure 2:
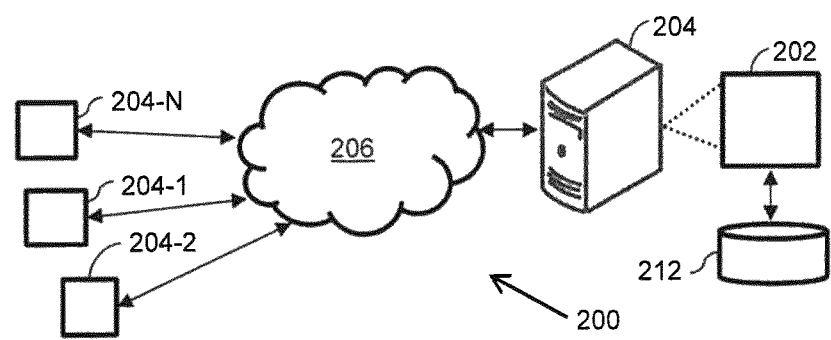
FIG. 2 is network implementation of system for PPG signal quality assessment according to some embodiments of the present disclosure.

Referring now to FIG. 2, a network implementation 200 of system 202 for PPG signal quality assessment is illustrated, in accordance with an embodiment of the present subject matter. The system 200 is adapted to assess the clinical usability of fingertip PPG waveform, collected from medical grade oximeter (train data) and smartphone (test data). In various embodiments, the system 202 utilizes a set of Signal Quality Indices (SQIs) to represent the noise characteristics of the PPG waveform/signal. The SQIs are presented to a Random Forest (RF) classifier to discriminate between clean and noisy signals, thereby assessing the quality if the PPG signal.

Although the present subject matter is explained considering that the system 202 is implemented for PPG signal quality assessment, it may be understood that the system 202 may is not restricted to any particular machine or environment. The system 202 can be utilized for a variety of domains where PPG signal quality assessment is to be determined. The system 202 may be implemented in a variety of computing systems, such as a laptop computer, a desktop computer, a notebook, a workstation, a mainframe computer, a server, a network server, a smart phone, a wearable device, and the like.

Herein, the system 202 may acquire PPG signal via devices and/or machines 204-1, 204-2 . . . 204-N, collectively referred to as devices 204 hereinafter. The devices 204 may include testing devices. In an embodiment, the testing devices may include handheld electronic device, a mobile phone, a smartphone, a portable computer, a PDA, and so on. Alternately or additionally, the devices 204 may include training devices such as a pulse oximeter. The devices 204 are communicatively coupled to the system 202 through a network 206, and may be capable of transmitting the captured PPG signal to the system 202.

In one implementation, the network 206 may be a wireless network, a wired network or a combination thereof. The network 306 can be implemented as one of the different types of networks, such as intranet, local area network (LAN), wide area network (WAN), the internet, and the like. The network 206 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 206 may include a variety of network devices, including routers, bridges, servers, computing devices, storage devices, and the like.

In an embodiment, the system 202 may be embodied in a computing device 210. Examples of the computing device 210 may include, but are not limited to, a desktop personal computer (PC), a notebook, a laptop, a portable computer, a smart phone, a tablet, and the like. The system 202 may also be associated with a data repository 212 to store at least data associated with the PPG signal. Additionally or alternatively, the data repository 212 may be configured to store data and/or information generated during quality assessment of the PPG signal. The repository 212 may be configured outside and communicably coupled to the computing device 210 embodying the system 202. Alternatively, the data repository 212 may be configured within the system 202. An example implementation of the system 202 for signal quality assessment of the PPG signal is described further with reference to FIG. 3.

Figure 3:
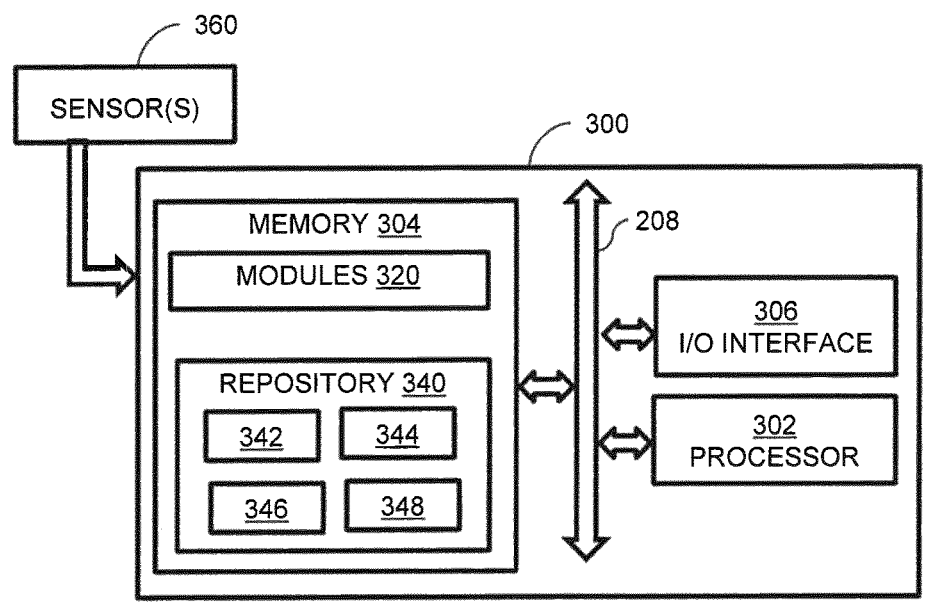
FIG. 3 illustrates a block diagram of a system for PPG signal quality assessment in accordance with some embodiments of the present disclosure.

FIG. 3 illustrates a block diagram of an exemplary system 300 for quality assessment of a PPG signal, in accordance with an example embodiment. The system 300 may be an example of the system 202 (FIG. 2). In an example embodiment, the system 300 may be embodied in, or is in direct communication with the system, for example the system 202 (FIG. 2). The system 300 includes or is otherwise in communication with one or more hardware processors such as a processor 302, at least one memory such as a memory 304, and an I/O interface 306. The processor 302, memory 304, and the I/O interface 306 may be coupled by a system bus such as a system bus 308 or a similar mechanism.

The hardware processor 302 may be implemented as one or more microprocessors, microcomputers, microcontrollers, digital signal processors, central processing units, state machines, logic circuitries, and/or any devices that manipulate signals based on operational instructions. Among other capabilities, the processor 302 is configured to fetch and execute computer-readable instructions stored in the memory 304.

The I/O interface 306 may include a variety of software and hardware interfaces, for example, a web interface, a graphical user interface, and the like The interfaces 306 may include a variety of software and hardware interfaces, for example, interfaces for peripheral device(s), such as a keyboard, a mouse, an external memory, a camera device, and a printer. Further, the interfaces 306 may enable the system 302 to communicate with other devices, such as web servers and external databases. The interfaces 306 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 306 may include one or more ports for connecting a number of computing systems with one another or to another server computer. The I/O interface 306 may include one or more ports for connecting a number of devices to one another or to another server.

The memory 304 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 304 includes a plurality of modules 320 and a repository 340 for storing data processed, received, and generated by one or more of the modules 320. The modules 320 may include routines, programs, objects, components, data structures, and so on, which perform particular tasks or implement particular abstract data types. Additionally, the other modules 320 may include programs or coded instructions that supplement applications and functions of the system 300. The repository 340, amongst other things, includes a system database 342 and other data 344. The other data 344 may include data generated as a result of the execution of one or more modules in the modules 320. Additionally, the repository 340 may include a sensor data 346 and a training data 348. The sensor data 346 may be obtained from one or more sensors 360 employed for physiological sensing of a subject. The sensor data 346 may include PPG signal samples obtained for training a model for PPG signal quality extraction. The training data 348 may be obtained based on training of a classifier for physiological monitoring of the subject. In an example embodiment, the physiological monitoring of the subject may be performed by acquiring PPG signals from the subject, by for example, fingertip of the subject. The details of the sensor data and the training data are explained further in the description below.

Herein, the memory for example the memory 304 and the computer program code configured to, with the hardware processor for example the processor 302, causes the system 300 to perform various functions described herein under.

As discussed above, for quality assessment of physiological signals such as PPG signals, the system 300 is caused to acquire or obtain physiological signals from the subject/user. In an embodiment, the PPG signals are captured from a testing device in real-time. Herein the testing device may refer to a device, for example a mobile electronic device embodying the sensors 360, and the PPG signals acquired from the testing device may refer to sensor data 346.

The system 300 segments the PPG signal into a first plurality of PPG signal samples. The length of each of the first plurality of PPG signal samples is more than a threshold length. In an embodiment, the threshold length is around 8 seconds with almost 50 percent overlapping. The overlapping of PPG signal samples is illustrated further in FIG. 17. Herein, for a real-time PPG signal quality assessment, the system 300 takes fixed small window based quality check instead of longer samples to reduce data drop and computation loss. However, for a PPG sample to retain sufficient information for analysis, a minimum window length must be adhered to. Considering the lowest human heart rate to be 40 beats (cardiac cycles) per minute i.e. 1.5 second per cycle and a minimum 4 such cycles (chosen heuristically) to observe morphological variation with maximum loss of 2 incomplete cycles (from start and end of the window), the window length may be assumed to be about 8 seconds. Therefore, the collected PPG signals (or datasets) are subdivided into the first plurality of PPG signal segments of 8 seconds window length. Said PPG signal segments may hereinafter be referred to as PPG signal samples, and any one sample of the PPG signal samples may be referred to as a first PPG signal sample.

The system 300 evaluates the first plurality of PPG signal samples to classify each of said signal samples as clean and noisy PPG samples. In order to classify the signal samples, the system 300 performs, for each of the signal sample, (1) a signal sufficiency check (SSC) of the sample, and (2)

Sample prediction using two class classification. The details of the SSC and sample prediction are explained further in the description below.

For performing the signal sufficiency check, the system 300 does a sanity check on the each of first PPG signal sample of the first plurality of signal samples to ensure that said first PPG signal sample has sufficient information for further processing of the real-time PPG signal quality assessment. In an embodiment, upon SSC, the system 300 obtains at least a first set of PPG signal samples complying with the SSC. In an embodiment, the system 300 employs two criterion for SSC check, namely (1) a clipping and flat signal distortion check, and (2) heart rate (HR) check, for a sample to be considered sufficient.

Figure 4:
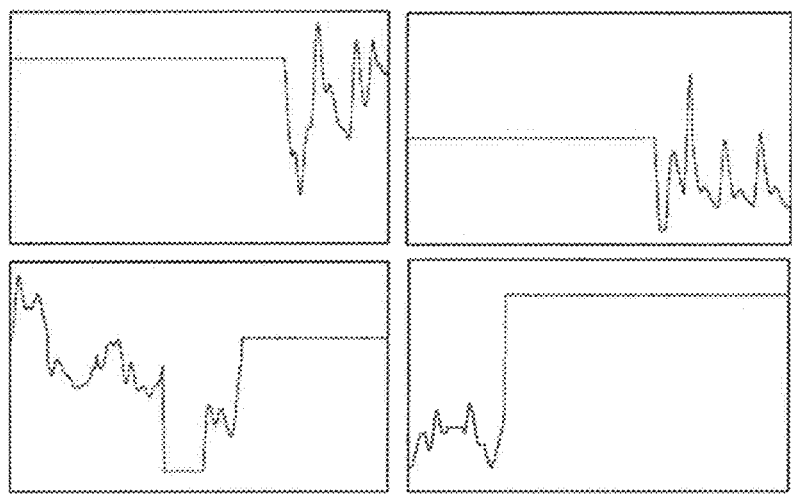
FIG. 4 PPG signal samples having flat signal in accordance with some embodiments of the present disclosure.

Clipped and flat signals are a form of waveform distortion that occurs when signal amplitude goes beyond the range restricted by a chosen representation and have constant amplitude level, respectively. Typical representation of flat and clipped signals is illustrated in FIG. 4. Presence of clipped or flat signal is undesirable while applying morphological operations, thus needs to be detected. The system 300 detects whether portions of the first PPG signal samples have maximum, minimum or constant amplitude values. If the system 300 detects that any such portion contributes more than a threshold value of length of the first PPG signal sample, then said first PPG signal sample is categorized as noisy.

The system 300 performs the HR check by determining whether a value of HR extrapolated from the first PPG signal sample lie between 40 and 150 cardiac cycles per minute (beats per minute). If the first PPG signal sample passes both the criteria of the clipping and flat signal distortion check, and the HR check, it is proceeded for template creation and further processing. However, if the first PPG sample fails to pass SSC in testing phase, it is predicted as noisy. Based on application of the SSC to the first plurality of PPG signal samples, the system 300 obtains at least the first set of PPG signal samples complying with the SSC.

Figure 5:
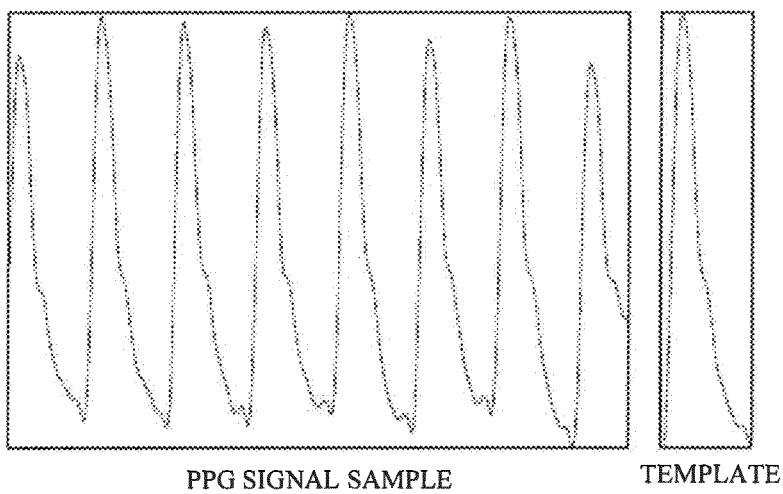
FIG. 5 illustrates a PPG signal samples with a corresponding template in accordance with some embodiments of the present disclosure.

The system 300 segments each of the first PPG signal samples into cardiac cycles using subsequent trough positions for template creation. Peaks and troughs of the filtered samples are detected using a threshold based approach. Superimposing cardiac cycles centering around the peaks reveal that despite the differences in base amplitude and pulse width, clean pulses taken from a short duration are almost identical morphologically, except when corrupted with artefacts. The proposed approach computes the median of all the cycles to create online template T. This ensures that T retains the most frequently occurring morphological features in the PPG signal sample as shown in FIG. 5

The system 300 extracts a set of features from the first set of PPG signal samples. The set of features represents an optimal set of features derived from a pre-stored training data by a training model during a training phase. During the training phase, the training model determines the set of features from amongst the plurality of features, where the plurality of features represents PPG based SQIs that can be potentially used for quality assessment of PPG signals. The derivation of the optimal set of features from the pre-stored training data by the training model during the training phase will be explained later in the description.

In an embodiment, plurality of features includes $SQI_1$ (Ratio of Cardiac diastole duration (td) to Ventricular systole duration (ts) are computed for a PPG cycle of the PPG signal sample), $SQI_2$ (ratio of summation of every complete PPG cycle length extracted from sample to the sample length), $SQI_3$ (mean of $DTW_{distance}$ of the sample), $SQI_4$ (Variance of the ratio P1height/P2height of every cycle in a sample), $SQI_5$ (variance of the kurtosis of every pulse), $SQI_6$ (ratio of max PP & min PP, where PP is peak to peak distance in a sample), $SQI_7$ (variance of amplitude ratio (amplitude of cycle/amplitude of T), $SQI_8$ (median of direct matching (Correlation Coefficient) between cycle and T), $SQI_9$ (variance of Pulse Width), and $SQI_{10}$ (variance of root mean square error of cycle and T). The plurality of features are explained hereinunder.

Figure 6:
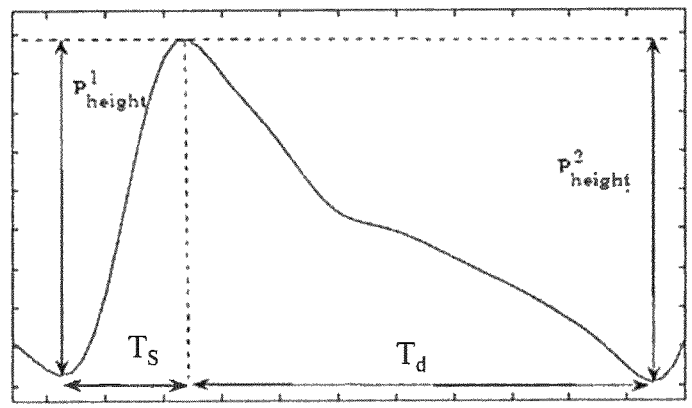
FIG. 6 illustrates a PPG signal sample with defined time domain features in accordance with some embodiments of the present disclosure.

$SQI_1$: The system 300 computes a ratio of Cardiac diastole duration ($t_d$) to Ventricular systole duration ($t_s$) for every PPG cycle in the sample, as shown in FIG. 6. PPG cycle must have $t_d > t_s$. The Cycle $t_d > t_s \subset$ Cycle are those cycles, thus $SQI1 = |Cycle_{td>ts}|/|Cycle|$. The intuition behind using this SQI is to find that ratio of actual PPG cycles present in the PPG signal sample.

$SQI_2$: Presence of signature which are not present in clean signal such as aperiodic signal and amplitude fluctuations (which may happen due to coronary perfusion pressure, motion artefacts, or variation in ambient lighting) are undesirable and thus need to be detected. The ratio of summation of every complete PPG cycle length extracted from sample to the sample length would be the clear indicator for the presence of such unwanted signal.

$$SQI_2 = \Sigma P \text{ duration (Cycle)/duration (Sample)}$$

$SQI_3$: PPG being a quasi periodic and inherently repetitive signal, Dynamic Time Warping (DTW) can be used to find an optimal match between two time series. The sequences are aligned or "warped" non-linearly in the time dimension to determine an optimal path. $DTW_{distance}$, the length of the optimal path, is calculated for every cycle in the sample from the template T. The mean of $DTW_{distance}$ of the sample is $SQI_3$.

$SQI_4$: Baseline variation is very common in PPG signal, where beat-to-beat low frequency fluctuation reflects mechanical consequence of respiration on venous return. The variation of the amplitudes due to baseline affects the morphology of the signal, thus for the stability check we take into account the peak heights from both preceding and succeeding trough of every cardiac cycles. Considering a PPG cycle having two troughs ($t_1$ and $t_2$) and a peak $p_k$ in between, as shown in FIG. 6, two pulse heights of a cycle $P_{height}^1$ (absolute height difference between $t_2$ and $p_k$), and $P_{height}^2$ (absolute height difference between $t_2$ and $p_k$) are calculated. Variance of the ratio $P_{height}^1/P_{height}^2$ of every cycle in a sample is $SQI_4$.

Figure 7:
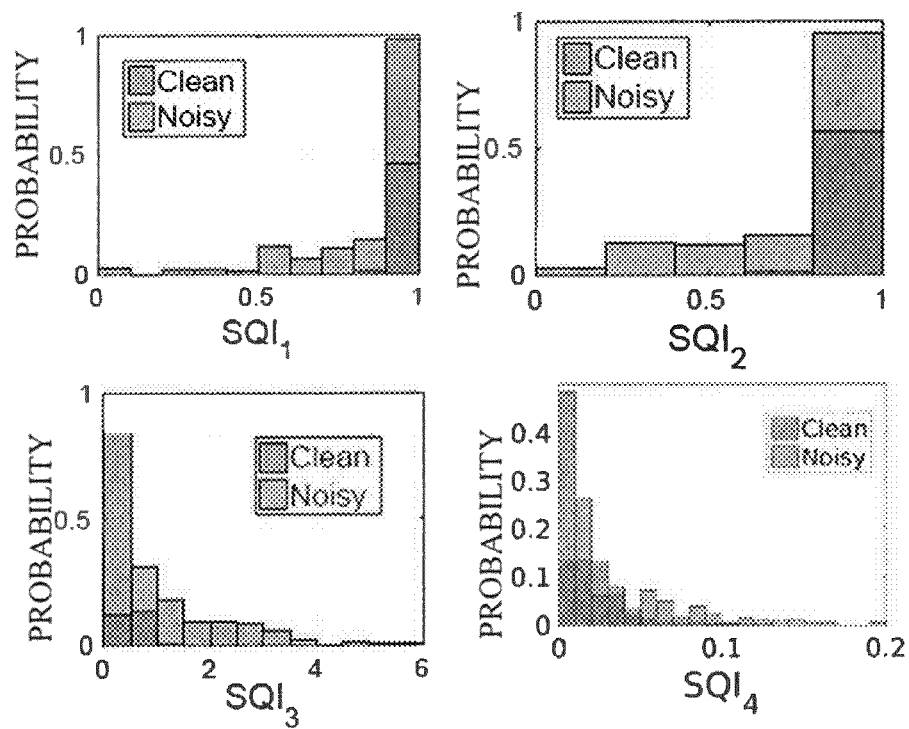
FIG. 7 illustrates Probability distribution of (a) $SQI_1$, (b) $SQI_2$, (c) $SQI_3$, and (d) $SQI_4$ over clean and noisy samples in accordance with some embodiments of the present disclosure.

An example probability distribution of SQIs numbered $SQI_1$ to $SQI_4$ over clean and noisy samples on training dataset are depicted in FIG. 7.

In addition to the features $SQI_1$-$SQI_4$, the system 300 computes additional features $SQI_5$-$SQI_{10}$, defined above.

The system 300 identifies, based on the set of features, each of the first PPG signal sample of the set of PPG signal samples as one of a noisy signal sample and a clean signal sample. In an embodiment, the system 300 utilizes a plurality of Random Forest (RF) models created during the training phase for identifying the first PPG signal samples as clean or noisy signal samples. Random Forest (RF) is an ensemble of decision trees, and is utilised by the system 300 for the assessment of PPG signal quality. RF classifier creates a bagging of decision trees where successive trees do not depend on earlier trees and are independently constructed using a bootstrap sample of the dataset. In the end, a simple ensembling method (majority voting) is executed for prediction, thereby avoiding an overfitted solution. The Random Forest model gives the output posterior probabilities which is in the range of 0 to 1. The system 300 classifies the signal with threshold 0.5. Signal with posterior probabilities greater than 0.5 are considered clean.

As described above, the system 300 is capable of training a model during a training phase for the quality assessment of PPG signal. The training phase is explained below in detail.

Training Phase

In an embodiment, the system 300 is caused to model a training model prior to performing the PPG signal quality assessment on the testing device. The system 300 obtains at least one training PPG signal captured from a training device. In an embodiment, the training device may include a pulse oximeter. The system segments the at least one training PPG signal into a second plurality of PPG signal samples. The system performs SSC for each second PPG signal sample of the second plurality of PPG signal samples to obtain a set of clean PPG signal samples complying with the SSC and a set of noisy PPG signal samples not complying with the SSC. Herein, the SSC check may be performed using the criteria that are used for SSC check during the testing phase. Hence, for the brevity of description, the details of SSC check are not explained herein. If any of second signal samples passes both the criteria, it is then proceeded for template creation (as previously explained) and further processing. However, if the sample fails to pass SSC in training phase, it is not considered for training the model.

The system 300 removes the PPG signal samples failing the SSC check, and considers only the PPG samples which are passed from SSC are used for creating training model. Supposing passed PPG signal samples contains 'N' noisy and 'C' clean samples, since N and C may not be equal, which can create a training model having bias towards the majority class. Therefore, the system 300 creates a subset of this dataset (containing the passed PPG signal samples), such that the majority class samples are divided into subsets having equal number of minor class samples. In an embodiment, the system 300 creates a plurality of sets of balance class subsets of the training data, where each set of balanced class subset includes the set of noisy PPG signal samples and equal number of randomly taken non overlapping clean PPG signal samples taken from the set of clean PPG signal samples. For example, if 100 samples are clean and 50 are noisy, the system 300 creates 2 subset of data having 50 clean and 50 noisy samples Herein, it will be noted that the system uses all noisy samples in both subset.

The system 300 utilises these subsets for ranking the features based on minimum-redundancy maximum-relevancy (mRMR). Herein, each balanced subset of data is considered for ranking of features. Due to configuration of the balanced data in said subset, system will not get biased on any class. Now, using each data in this subset, the system evaluates all of the plurality of SQIs. Applying mRMR on said features list (i.e. number of data*number of SQIs), the system generates ranks of each SQIs. The process is repeated for remaining balanced subset to get ranking of the SQIs. For the example the disclosed system has 7 balanced subset, thus there are 7 sets of ranking for SQIs. Now a mean of said rankings is taken each SQIs to get the overall ranking. Based on this ranking, feature selection is done, as explained below.

Further, the system 300 averages features ranks for all the subsets to find a single rank for each features. Based on said rank, an internal cross-validation is performed to find the optimal number of features based on their ranks taken cumulatively. For example, in case of 10 ranked features, at first step the system considers only one feature which has rank 1 to find the accuracy. From next step, the system 300 adds feature with rank 2, thus the system 300 considers 2 features now, and calculates the new accuracy. The process of cumulatively adding the features and computing new accuracy is repeated till the last ranked feature, so that in the end there are 10 sets of accuracies. The system 300 determines the features that give higher and stable accuracy. For example, in an example scenario, it may be at 9th index (ie top 9 features considered). Therefore, top 9 ranked features are considered for the creation of the training model. An example flow diagram for signal quality assessment of a PPG signal is described and illustrated with reference to FIG. 8.

Figure 8:
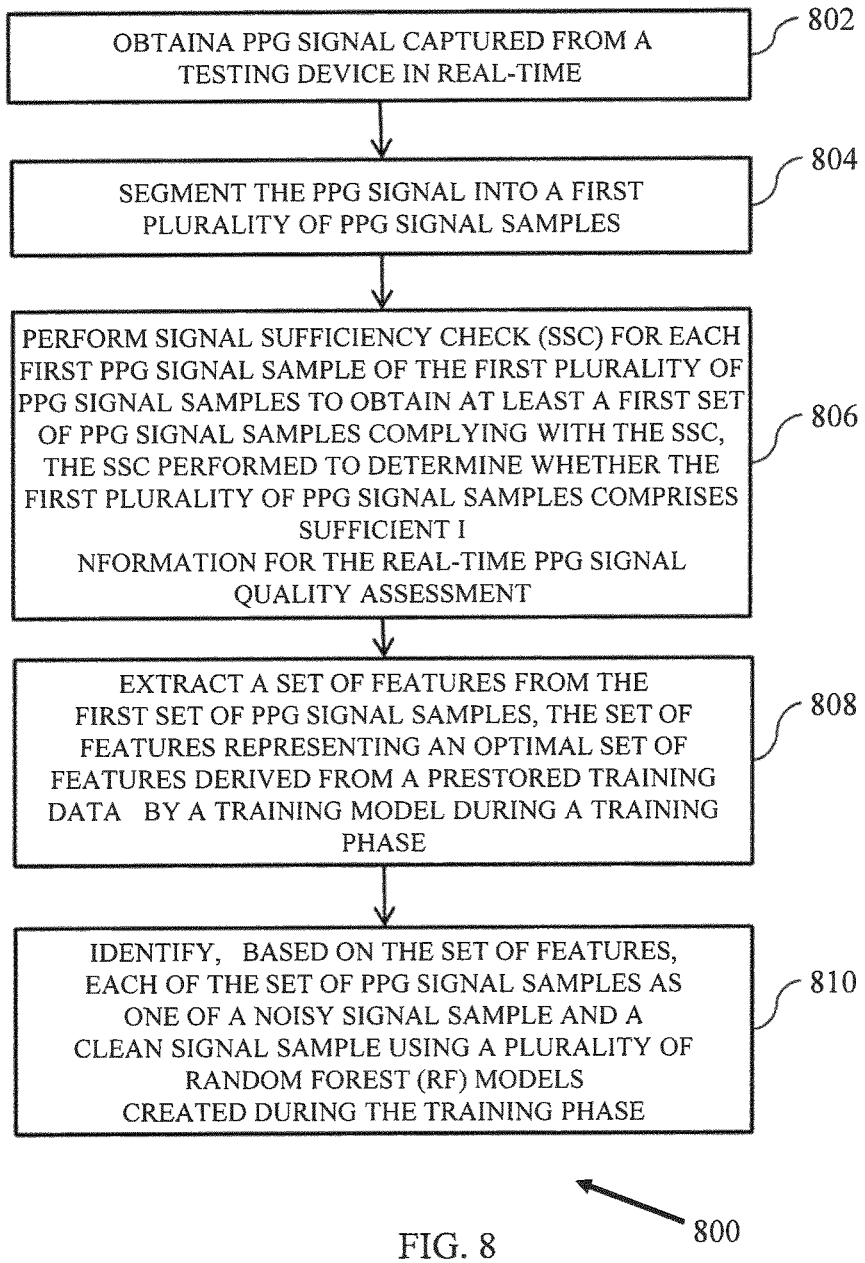
FIG. 8 illustrates an example flow diagram representing a method for PPG signal quality assessment in accordance with some embodiments of the present disclosure.

FIG. 8 illustrates a flow diagram of a method 800 for quality assessment of a PPG signal, according to some embodiments of the present disclosure. The method 800 may be described in the general context of computer executable instructions. Generally, computer executable instructions can include routines, programs, objects, components, data structures, procedures, modules, functions, etc., that perform particular functions or implement particular abstract data types. The method 800 may also be practiced in a distributed computing environment where functions are performed by remote processing devices that are linked through a communication network. The order in which the method 800 is described is not intended to be construed as a limitation, and any number of the described method blocks can be combined in any order to implement the method 800, or an alternative method. Furthermore, the method 800 can be implemented in any suitable hardware, software, firmware, or combination thereof. In an embodiment, the method 800 depicted in the flow chart may be executed by a system, for example, the system 302 of FIG. 3. In an example embodiment, the system 302 may be embodied in an exemplary computer system.

Referring to FIG. 8, in the illustrated embodiment, the method 800 is initiated when at 802, obtaining a PPG signal captured from a testing device in real-time. In an embodiment, PPG signal is obtained from a testing device for instance a smartphone. At 804, the method 800 includes segmenting the PPG signal into a first plurality of PPG signal samples. Herein, the length of each of the first plurality of PPG signal samples more than a threshold length. In an example embodiment, the threshold sample length may be around 8 seconds, as is already explained with reference to FIG. 3.

At 806, the method 800 includes performing SSC for each first PPG signal sample of the first plurality of PPG signal samples to obtain at least a first set of PPG signal samples complying with the SSC. The SSC performed to determine whether the first plurality of PPG signal samples comprises sufficient information for the real-time PPG signal quality assessment. The details of SSC are explained with reference to FIGS. 3 and 4.

At 808, the method 800 includes extracting a set of features from the first set of PPG signal samples. The set of features represents an optimal set of features derived from a prestored training data by a training model during a training phase. At 810, the method 800 includes identifying, based on the set of features, each of the set of PPG signal samples as one of a noisy signal sample and a clean signal sample using a plurality of Random Forest (RF) models created during the training phase. An example process flow for the quality assessment of the PPG signals is explained further with reference to FIG. 9.

Figure 9:
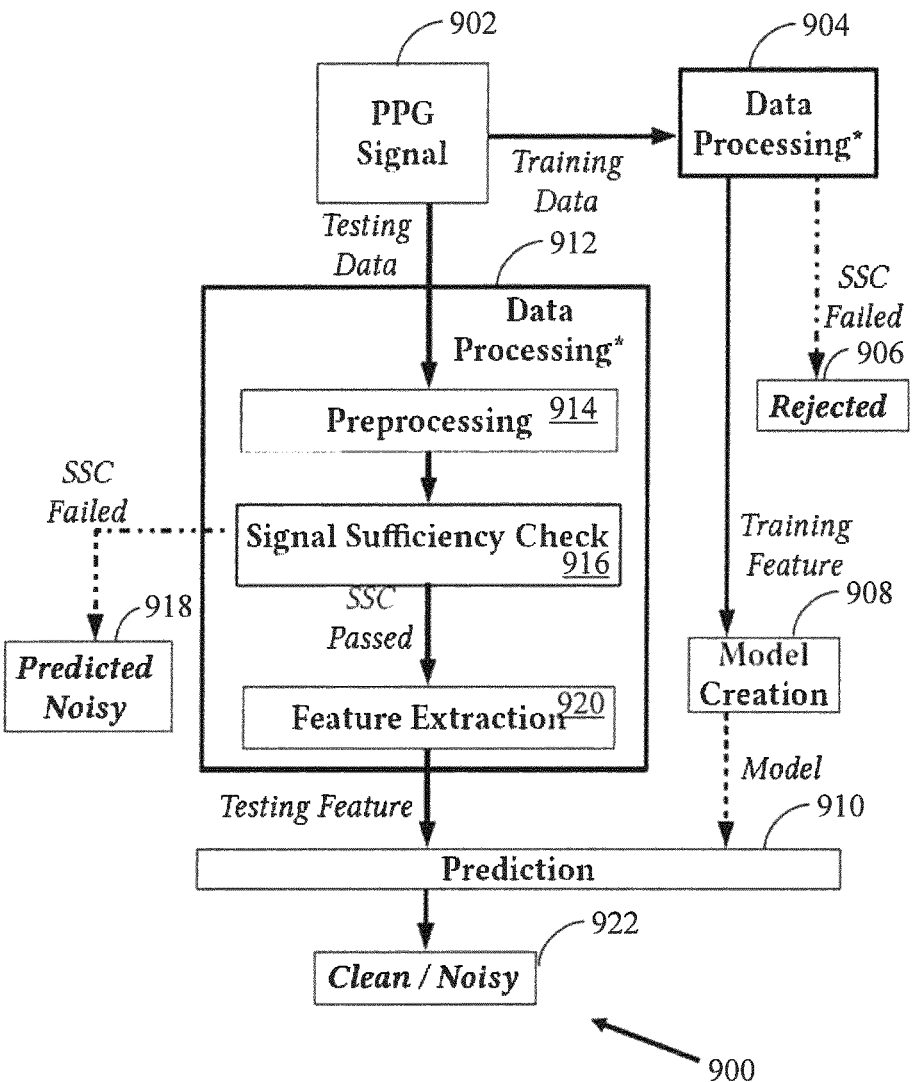
FIG. 9 is an example process flow for PPG signal quality assessment in accordance with some embodiments of the present disclosure.
Figure 12:
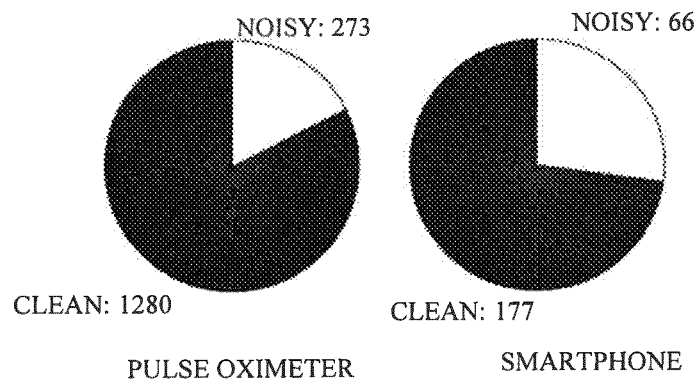
FIG. 12 illustrates an example distribution of clean and noisy signal samples for PPG signal quality assessment in accordance with some embodiments of the present disclosure.

FIG. 9 illustrates a process flow 900 for quality assessment of PPG signals, in accordance with an example embodiment. The process flow includes two stages: a training stage and a testing stage. During the training stage, a model is trained for performing quality assessment of PPG signals. During the testing stage the trained model is utilized for predicting the probabilities of PPG samples to be clean or noisy. A stepwise process flow for training and testing stages is presented below.

During the training stage, PPG signals 902 are obtained from a training device, for example a pulse oximeter. The PPG signals obtained from the training device may be referred to as a training data. The training data is preprocessed at 904 by segmenting the PPG signal into a second plurality of PPG signal samples, such that the length of each of the second plurality of PPG signal samples is more than a threshold length. In an embodiment, the threshold length is around 8 seconds with almost 50 percent overlapping. A check, called signal sufficiency check (SSC) is applied on each of the first PPG signal sample of the second plurality of signal samples to ensure that said first PPG signal sample has sufficient information for further processing of the real-time PPG signal quality assessment. As previously explained the SSC includes criterion namely, (1) a clipping and flat signal distortion check, and (2) heart rate (HR) check, for a sample to be considered sufficient. The details of the SSC check are already described with reference to FIGS. 3 and 4. If any of second signal samples passes both the criteria, it is then proceeded for template creation (as previously explained) and further processing. However, if the sample fails to pass SSC in training phase, it is not considered for training the model and is rejected as noisy at 906. The second signal samples passing the SSC check are considered for feature extraction and model creation at 908. So, the PPG signal samples failing the SSC check are removed, and only the PPG samples which are passed from SSC are used for feature extraction and creating training model. The training model is utilized for predicting whether the testing PPG signal samples are clean or noisy.

During the testing stage, the testing data containing PPG signals is obtained from a testing device for example, from a wearable electronic device such as a smart watch. The testing data containing the PPG signals is pre-processed at 912, wherein during the pre-processing stage at 914 the PPG signal is split into a first plurality of signal samples. Said signal samples are checked for SSC at 916. The signal samples failing the SSC are predicted as noisy at 918. However, the signal samples passing the SSC check are utilized for feature extraction at 920. Various SQIs have been disclosed that are utilized as features. In an embodiment, a optimal set of features selected during the training stage are considered as testing features during the testing stage. The testing features are utilized for prediction of the signal samples as noisy or clean at 922, as is described with reference to FIG. 3 previously. An example scenario for quality assessment of PPG signals is described further with reference to FIGS. 10A-19B.

Example Scenario:

For determining quality assessment of the PPG signals in accordance with embodiments disclosed herein, PPG waveforms from multiple sensor sources are obtained, and utilized to find sensor agnostic SQIs. Datasets are created comprising 1) the ICU unit of an urban hospital in India and 2) a basic healthcare unit of an Indian village. In the first case, PPG signals are collected using Pulse oximeter (Contec CMS 50D+2) at 60 Hz of sampling rate while the 2nd PPG dataset are collected using an in-house smartphone video camera app to capture red component of the rgb frames at fixed frame per second of 24 Hz. All PPG signals are collected from the right hand index finger of every subjects, as shown in FIGS. 9 and 10. A total of 85 subject's (Pulse oximeter: 35 and Smartphone: 50) data are captured having diverse age, weight, height and clinical conditions in a stable sitting posture. For collecting data, the permission from the Institutional Review Board (IRB) and the written consent of the subjects are taken.

Analyzing the datasets, annotators found that smartphone camera based PPG signal is more prone to jitter caused by random noise and motion artefacts. While pulse oximeter based PPG signals have significantly clean morphology, however with plenty of flat and clipped portions due to intermittent signal loss. Considering prevalent noise pattern differences in the datasets, finding out a common set of SQIs for quality check is a challenge. Smartphone data being significantly prone to noise, as formerly explained and shown in FIG. 1, are considered as hidden test dataset for evaluating embodiments while pulse oximeter data is used as training dataset.

For a real-time PPG signal quality assessment, fixed small window based quality check are taken instead of longer samples to reduce data drop and computation loss. However, for a PPG sample to retain sufficient information for analysis, a minimum window length must be adhered to. Considering the lowest human heart rate to be 40 beats (cardiac cycles) per minute i.e. 1.5 second per cycle and a minimum 4 such cycles (chosen heuristically) to observe morphological variation with maximum loss of 2 incomplete cycles (from start and end of the window), the window length is kept to be 8 sec. Therefore, the collected PPG datasets are sub-divided into multiple chunks of 8 seconds window length which resulted into 1553 samples from pulse oximeter and 243 samples in Smartphone dataset. These 8 sec PPG signal chunk are cited as "sample" in the description presented herein.

A graphical user interface is built on Matlab GUIDE software as shown in FIG. 11 for manual annotation. Four expert annotators are presented with filtered PPG samples to be assessed one at a time. Bandpass filtering is done on the PPG samples with the cutoff frequencies of 0.5 to 6 Hz using Butterworth filter. Thereafter, PPG waveform patterns are analyzed and classified into two discrete quality levels: 'Clean' and 'Noisy'. For scoring purposes, a 'radio button' facility is provided in the GUI as a tool to assist the scorers in assigning the pulses to an appropriate quality class. Following are the set of criteria annotators considered for a PPG sample to be clean.

- every cardiac cycle in the sample have similar morphological pattern,
- every cardiac cycle in the sample have distinct primary peak and troughs,
- sample does not contain clipping, and
- absence of any broken and unwanted non PPG signal.

A total of 1796 samples are randomly shuffled (to reduce bias over consecutive waveform while annotation) and annotated 'Clean' or 'Noisy'. The annotation is a subjective decision making process, thus final annotation is developed based on majority voting of annotations done by experts. A sample annotated clean and noisy twice is not taken into consideration. Out of 1553 samples 272 are labeled as corrupt or noisy in oximeter dataset while in smartphone dataset 66 out of 224 samples are labeled as noisy, also depicted by a pie chart in FIG. 12. Inter Rater Agreement—shows the correlation of 0.9359±0.05 from all the 6 combinations of 4 sets of annotations.

Post development of the annotation process, the PPG samples are classified by the system for instance the system 300 (of FIG. 3) using the method 800 (of FIG. 8), to classify clean and noisy PPG samples. The hierarchical decision making approach includes combining heuristics and machine learning technique, ordered below:
Sufficiency check of the sample, and
Sample prediction using two class classification.

Figure 13:
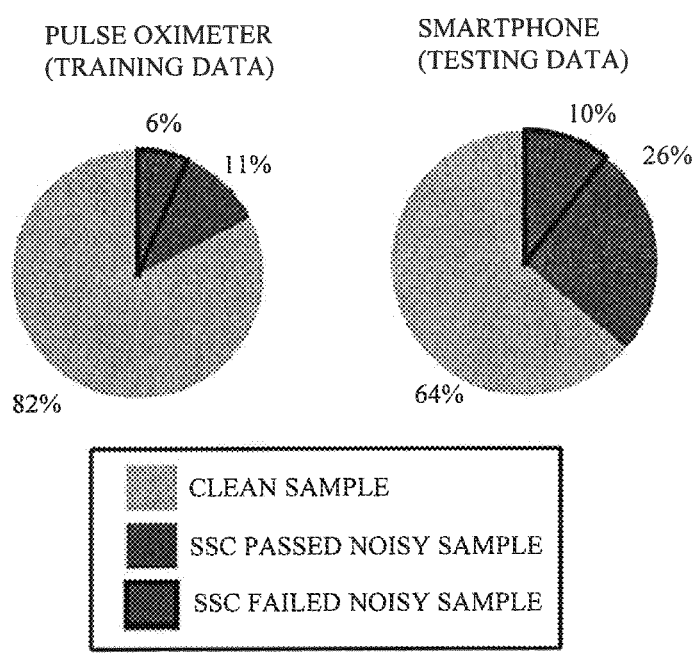
FIG. 13 illustrates an example SSC performance on train and test dataset for PPG signal quality assessment in accordance with some embodiments of the present disclosure.

As previously described, the system 300 is configured to perform SSC on train and test datasets to remove PPG samples which are insufficient to analyze. It is observed that none of the clean PPG samples have failed the SSC block in both datasets, as shown in FIG. 13. Since the annotation of PPG samples is not done on the basis of completeness or sufficiency parameters uniquely, the evaluation is only done on the factor whether any clean sample has been failed by this block or not. Out of 273 noisy samples present in train dataset 99 failed in SSC, and are not considered for training. While on other hand 19 of 66 noisy samples in test dataset have failed SSC block, and are classified as noisy. After removing the SSC failed samples, training dataset is left with 1280 clean and 174 noisy samples, while testing dataset have 177 clean and 47 noisy samples remaining, as shown in FIG. 13.

Considering the SQIs described in FIG. 3, the system determines optimal set of SQIs for assessing the quality of PPG sample, which are not redundant, reduces computation time, produces high and low variance performance. SQIs are therefore ranked based on Minimum Redundancy Maximum Relevance (mRMR) strength computed against the data class on training dataset. However, SSC passed training dataset is highly imbalance (Clean: Noisy class ratio 7:1), which will not give a holistic view of the SQIs correlation over data class. Thus a total of seven sets of balance class subsets of training dataset each containing all noisy samples and equal number of randomly taken non overlapping clean class samples are created. For each of the seven subsets the system computed ranks based on mRMR strengths of SQIs individually.

The final rank shown in Table 2 is calculated by ranking the mean of rank sets over every subset. The final rank is correlated to initial seven sets of rank series using Spearman's Rank Correlation Coefficients, with mean value 0.96, range [0.94, 0.98] and standard deviation of 0.01. Selection of optimal set of SQIs is done using internal performance evaluation; here top n SQIs (Table 2), iterated from 1 to 10, are trained and validated using 5-fold in training dataset to find the optimal value of n having high and stable performance metrics.

TABLE 2

| | SQI Index | | | | | | | | | |
|---|---|---|---|---|---|---|---|---|---|---|
| | 1 | 2 | 3 | 4 | 5 | 6 | 7 | 8 | 9 | 10 |
| Rank | 3 | 2 | 1 | 6 | 10 | 4 | 7 | 5 | 9 | 8 |
| STD | 0 | 0 | 0 | 1.5 | 0 | 0.4 | 1.5 | 0 | 0.8 | 0.8 |

Figure 14A:
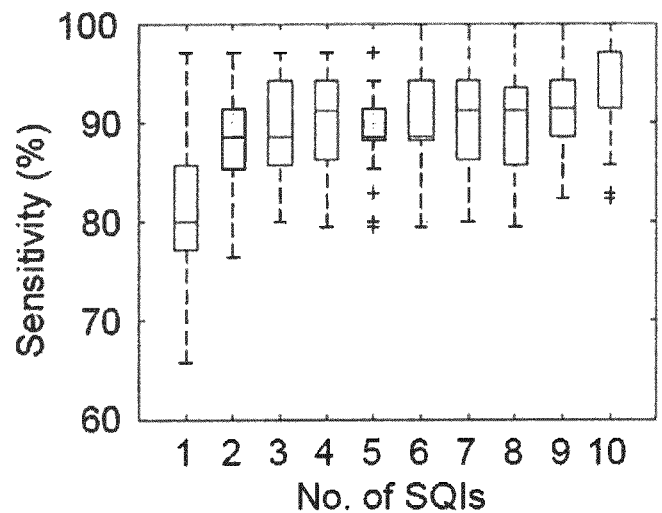
FIGS. 14A and 14B illustrate Mean (a) Sensitivity and (b) Specificity across 5-folds over 7 balanced subsets in accordance with some embodiments of the present disclosure.
Figure 14B:
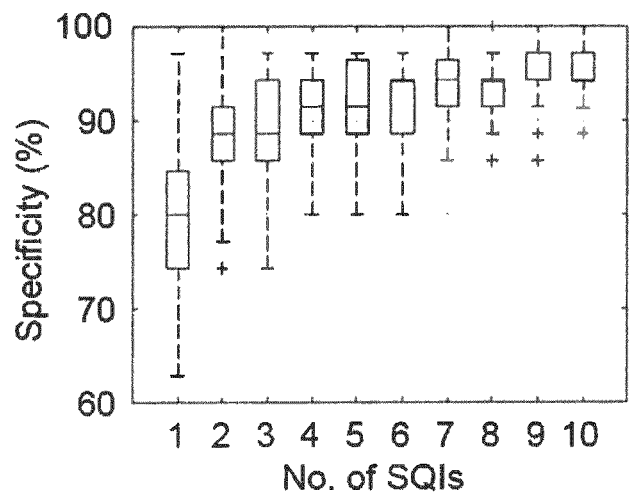

In FIGS. 14A and 14B, 5-fold performances on 7 subsets are depicted (edge of the boxes represent interquartile range), where x-axis represent the top n SQI set taken cumulatively. Proceeding thus, it is found that the optimum value of n for best performance, in terms of specificity is at n=9 and sensitivity is at n=5. Since the major focus is to predict noisy class correctly (i.e. high specificity), thus sensitivity is traded-off to select n=9. Therefore, top 9 SQIs from Table 2, which includes all the proposed SQIs, are considered for evaluation hereafter.

Considering a null hypothesis that the noisy and clean PPG samples comes from the distributions having equal mean, unpaired two sample t-test (Welch's t-test) is performed on selected SQIs over clean and noisy class population of test dataset, accounting for unequal variance. Differences are considered statistically significant at P<0.05. From Welch's t-test result shown in Table 3, it is observed that all the SQIs except $SQI_2$ failed the null hypothesis (p-value of $SQI_2$>0.05), in other words only $SQI_2$ is not able to differentiate between clean and noisy class in smartphone dataset within 5% significance level.

TABLE 3

| SQIs | p-value |
|---|---|
| $SQI_1$ | $1.4 * 10^{-12}$ |
| $SQI_2$ | 0.32 |
| $SQI_3$ | $5 * 10^{-18}$ |
| $SQI_4$ | $8.5 * 10^{-07}$ |
| $SQI_6$ | $9 * 10^{-07}$ |
| $SQI_7$ | 0.0015 |
| $SQI_8$ | $3.2 * 10^{-14}$ |
| $SQI_9$ | 0.0121 |
| $SQI_{10}$ | $2.6 * 10^{-04}$ |

Figure 15:
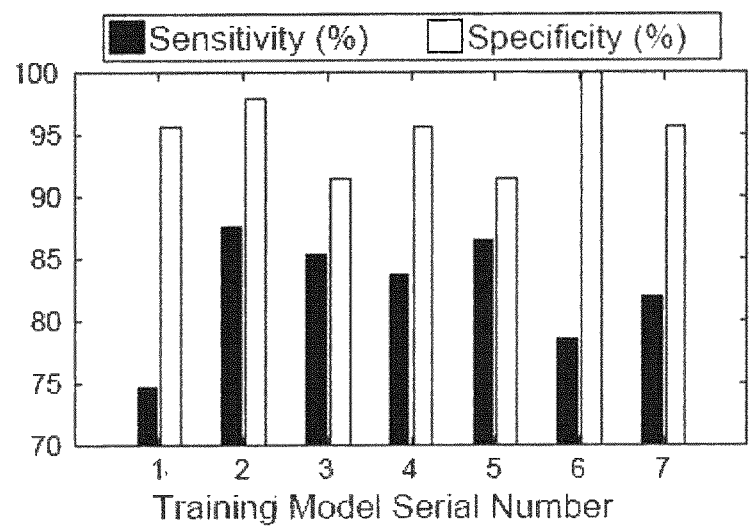
FIG. 15 illustrates example graph for sensitivity and specificity of 7 predictor models on the test dataset in accordance with some embodiments of the present disclosure.

The embodiments disclosed herein are evaluated in multiple scenarios, including an offline scenario and an online scenario. In offline scenario, Random Forest models are created for each of the 7 balanced subsets (as explained in Section 4.2) over the selected SQIs. Prediction on the test dataset is done using these 7 models and the result is shown in FIG. 15, where mean and standard deviation of sensitivity are 82.6% and 4.6% while mean and standard deviation of specificity are 95.4% and 3.1%.

Figure 16:
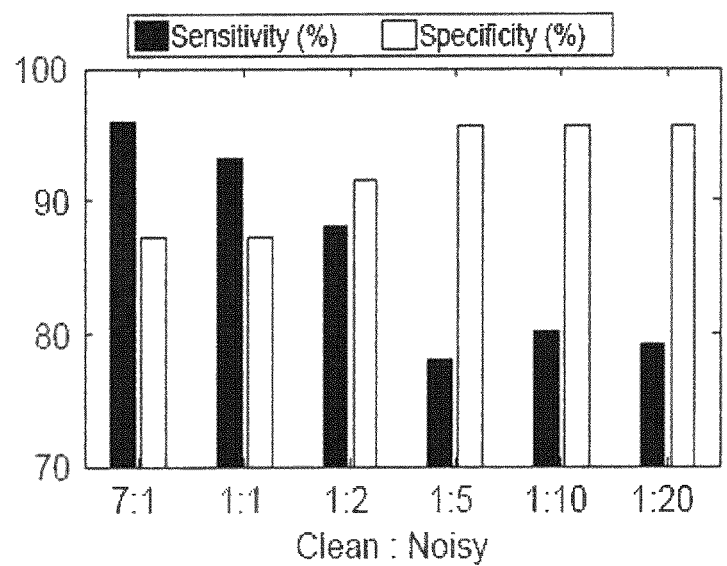
FIG. 16 illustrates an example graph for sensitivity and Specificity of 6 predictor models (trained using multiple class ratios by upsampling noisy class in training dataset) evaluated on test dataset in accordance with some embodiments of the present disclosure.

The classifier is also trained using the entire unbalanced (7:1) training dataset and then evaluated on the testing dataset to check the influence of majority class. This resulted to sensitivity and specificity of 96% and 87%, respectively. A SMOTE (Synthetic Minority Over-Sampling Technique) analysis is performed to test the stability of classifier by varying the ratio of clean and noisy class in training dataset. SMOTE upsamples the minor class from its population distribution using K-Nearest Neighbor (KNN) method. As shown in FIG. 16, when we gradually try to upsample the noisy samples in the training dataset, increase in specificity is observed. However, there is a drop in sensitivity by 10% while the noisy dataset is increased to 20 times that of clean samples. With mere 5% of clean instances in new training dataset, the disclosed system is still able to correctly classify 140 out of 177 clean samples. This proves that the system 300 is not getting biased to the majority class.

Figure 17:
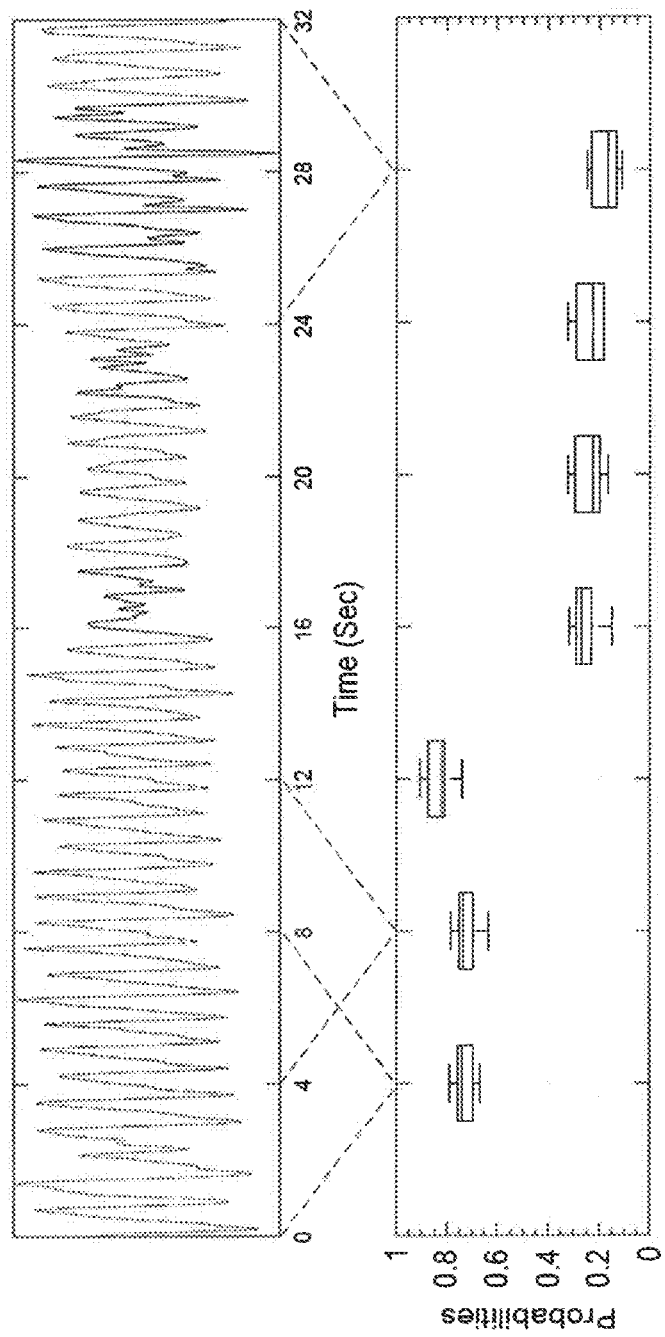
FIG. 17 illustrates posterior probabilities (clean:1 and noisy:0) of PPG quality computed on smartphone PPG signal, considering 8 sec window length with 50% overlap in accordance with some embodiments of the present disclosure.

Another scenario, which is an online scenario, a real-time analysis over the portion of PPG signal is recorded separately using smartphone to observe the performance of the classifier. A 32 seconds long continuous signal is taken, as shown in FIG. 17 with experts annotated noisy portion and partitioned into 8 second windows with 50% overlapping. The 7 predictors are then used for classification of these PPG samples. Posterior probabilities, probability of sample to be classified as clean, are evaluated wherein, the value of more than 0.5 is classified as clean class. The range of predicted posterior probabilities for every PPG sample is observed to be very small in FIG. 17, which shows high confidence of the predictors. Introduction of even small artefact in $4^{th}$ window lead decision to be in favour of noisy class. $3^{rd}$ window being visually highly stable and clean in morphology—predicted probabilities are highest too. While the last window, with majority portion annotated as noisy, shows the lowest score. This, thus proves that the disclosed system is reliable on field.

Figure 18:
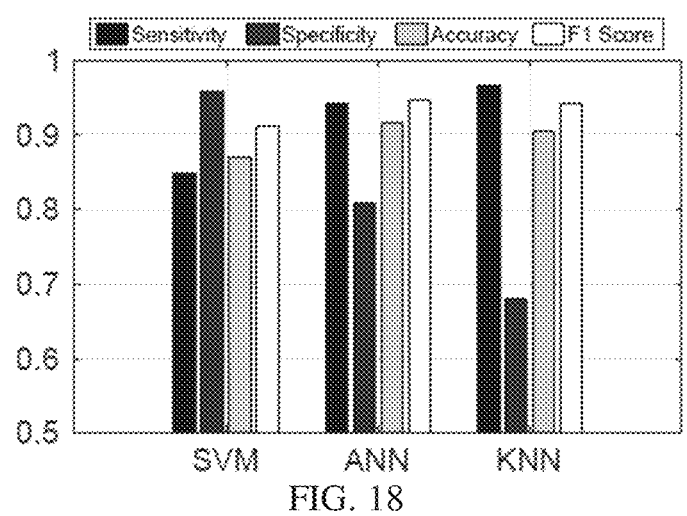
FIG. 18 illustrates example support vector machine (SVM), artificial neural network (ANN), and k-nearest neighbor (KNN) classifiers prediction on test dataset in accordance with some embodiments of the present disclosure.

Some other standard classifiers are also used for analyzing the goodness of the SQIs, including Support Vector Machine (linear SVM), Artificial Neural Network (ANN) with 1 hidden layer having 6 hidden nodes (chosen using internal cross validation), and K-Nearest Neighbor (Parameter: $k=(N)^{1/2}$, where N is number of samples in training dataset). Individually each classifiers are trained on the whole unbalanced (7:1) training data and then tested on the testing data. As seen in FIG. 18, none of the classifiers are giving less than 90% F1 score. The high performance metrics shows that our SQIs are true representative of quality indices.

The results obtained using the disclosed system is compared with the conventional systems, as is described below. Evaluation is done in two phases, using the methodology defined pertaining to the conventional methods; and secondly, using a classification technique (using SQIs defined pertaining to conventional methods) to observe the improvement. In certain conventional methods, heuristically taken threshold for SQIs are not provided, therefore said thresholds are evaluate using the classification method defined by the disclosed embodiments for a smartphone dataset. Here, both heuristic and machine learning approaches have considered heuristically determined threshold on SQIs to classify the PPG signal as clean and noisy. As expected, without good noise check, all three state of the arts are biased towards a single class, which proves that heuristically taken SQIs threshold values fails to work in sensor agnostic environment.

Figure 19A:
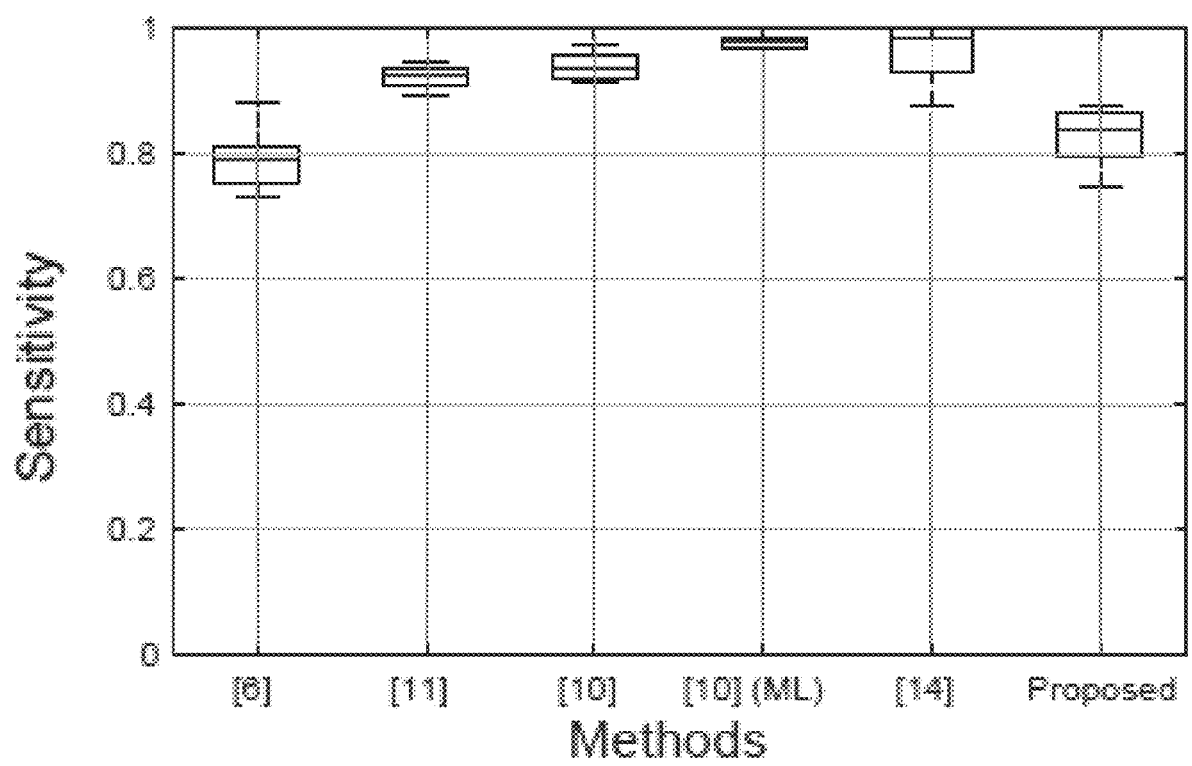
FIGS. 19A and 19B illustrate variation of example sensitivity and specificity, respectively obtained from conventional and disclosed PPG signal quality assessment method (implemented using RF classifier) in accordance with some embodiments of the present disclosure.
Figure 19B:
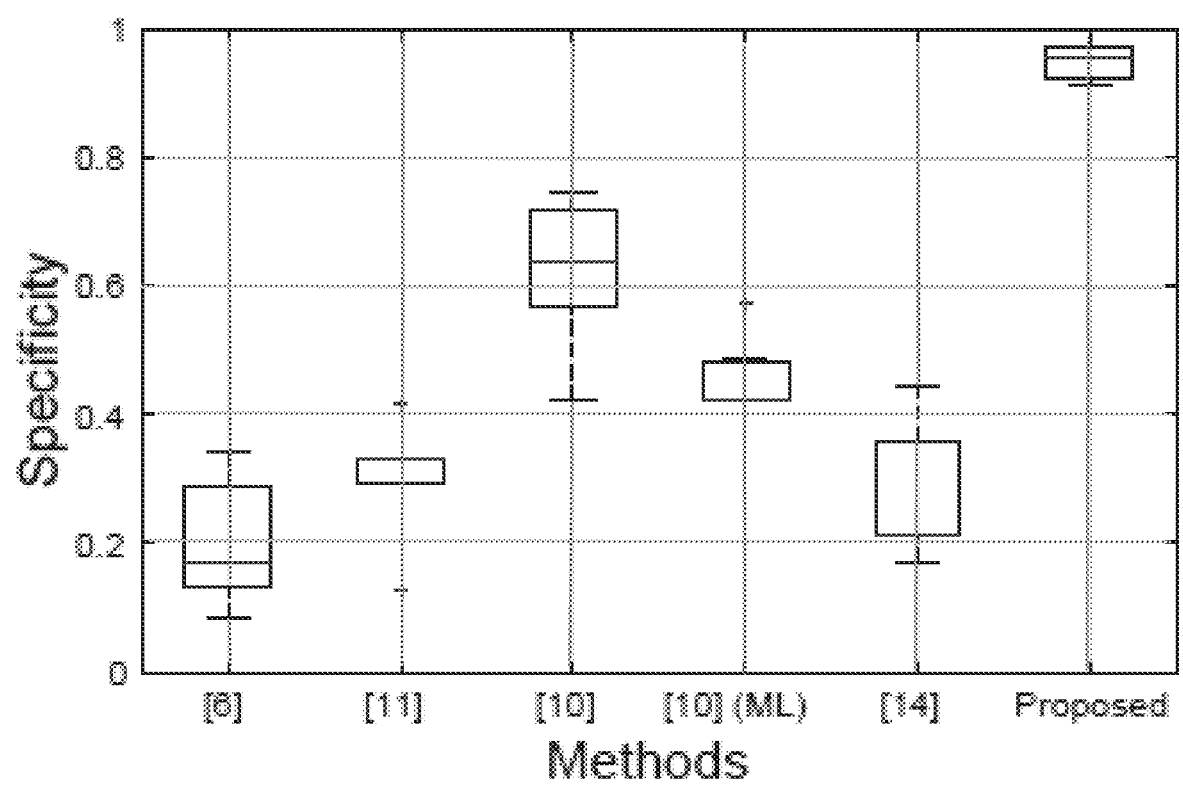

On the other hand, RF classifier is used for all methods to train on oximeter and test on smartphone data to observe robustness of SQIs across sensors, shown in FIGS. 19A and 19B. All prior arts tend to have biasness over majority class, resulting into very high sensitivity and low specificity. As evident in FIG. 19A, the disclosed method shows stable and high metrics. Though the sensitivity is marginally low compared to some methods, specificity is however significantly high. On top of that one may notice the small standard deviation in specificity (FIG. 19B) which makes the proposed system far more reliable compared to the state of the art methods.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for PPG signal quality assessment, comprising:
    obtaining a PPG signal captured using a testing device in real-time, via one or more hardware processors;
    segmenting, via the one or more hardware processors, the PPG signal into a first plurality of PPG signal samples, length of each of the first plurality of PPG signal samples more than a threshold length;
    performing, via the one or more hardware processors, signal sufficiency check (SSC) for each first PPG signal sample of the first plurality of PPG signal samples to obtain at least a first set of PPG signal samples complying with the SSC, the SSC performed to determine whether the first plurality of PPG signal samples comprises sufficient information for the real-time PPG signal quality assessment;
    extracting a set of features from the first set of PPG signal samples, via the one or more hardware processors, the set of features representing an optimal set of features derived from a pre-stored training data by a training model during a training phase; and
    identifying, based on the set of features, each of the set of PPG signal samples as one of a noisy signal sample and a clean signal sample using a plurality of Random Forest (RF) models created during the training phase, via the one or more hardware processors.

2. The method of claim 1, wherein the threshold sample is around 8 seconds.

3. The method of claim 1, wherein performing the SSC for a first PPG signal sample of the first plurality of PPG signal samples comprises:
    performing a clipping and flat signal distortion check, wherein the clipping and flat signal distortion check comprises detecting portions of the first PPG signal sample having maximum, minimum or constant amplitude value, and determining if any such portion contributes more than a threshold value of length of the first PPG signal sample then the first PPG signal sample is categorized as noisy, and
    performing a heart rate (HR) check, wherein the HR check comprises determining whether a value of HR extrapolated from the first PPG signal sample lie between 40 and 150 cardiac cycles per minute (beats per minute).

4. The method of claim 1, wherein modeling the training model comprises:

obtaining at least one training PPG signal captured from using a training device; segmenting the at least one training PPG signal into a second plurality of PPG signal samples, length of each of the second plurality of PPG signal samples more than the threshold length;

performing SSC for each second PPG signal sample of the second plurality of PPG signal samples to obtain a set of clean PPG signal samples complying with the SSC and a set of noisy PPG signal samples not complying with the SSC;

creating a plurality of sets of balance class subsets of the training data, each set of balanced class subset comprising the set of noisy PPG signal samples and equal number of randomly taken non overlapping clean PPG signal samples taken from the set of clean PPG signal samples;

computing a rank for each of the plurality of set of balanced class subsets based on a mRMR strengths of each of the plurality of features; and ranking a mean of rank sets over every subset to obtain the set of features.

5. The method of claim 4, wherein the training device comprises an oximeter.

6. The method of claim 1, wherein the plurality of features comprises:

SQI1 (Ratio of Cardiac diastole duration (td) to Ventricular systole duration (ts) are computed for a PPG cycle of the PPG signal sample), SQI2 (ratio of summation of every complete PPG cycle length extracted from sample to the sample length), SQI3 (mean of DTW distance of the sample), SQI4 (Variance of the ratio P1height/P2height of every cycle in a sample), SQI5 (variance of the kurtosis of every pulse), SQI6 (ratio of max PP & min PP, where PP is peak to peak distance in a sample), SQI7 (variance of amplitude ratio (amplitude of cycle/amplitude of T), SQI8 (median of direct matching (Correlation Coefficient) between cycle and T), SQI9 (variance of Pulse Width), and SQI10 (variance of root mean square error of cycle and T).

7. The method of claim 1, wherein the testing device comprises a smartphone.

8. A system for PPG signal quality assessment, the system comprising:

one or more memories; and one or more hardware processors, the one or more memories coupled to the one or more hardware processors, wherein the one or more hardware processors are capable of executing programmed instructions stored in the one or more memories to:

obtain a PPG signal captured using a testing device in real-time;

segment the PPG signal into a first plurality of PPG signal samples, length of each of the first plurality of PPG signal samples more than a threshold length;

perform signal sufficiency check (SSC) for each first PPG signal sample of the first plurality of PPG signal samples to obtain at least a first set of PPG signal samples complying with the SSC, the SSC performed to determine whether the first plurality of PPG signal samples comprises sufficient information for the real-time PPG signal quality assessment;

extract a set of features from the first set of PPG signal samples the set of features representing an optimal set of features derived from a pre-stored training data by a training model during a training phase; and identify, based on the set of features, each of the set of PPG signal samples as one of a noisy signal sample and a clean signal sample using a plurality of Random Forest (RF) models created during the training phase.

9. The system of claim 8, wherein the threshold sample length is around 8 seconds.

10. The system of claim 8, wherein to perform the SSC for a first PPG signal sample of the first plurality of PPG signal samples, the one or more hardware processors are further configured by the instructions to:

perform a clipping and flat signal distortion check, wherein the clipping and flat signal distortion check comprises detecting portions of the first PPG signal sample having maximum, minimum or constant amplitude value, and determining if any such portion contributes more than a threshold value of length of the first PPG signal sample then the first PPG signal sample is categorized as noisy, and perform a heart rate (HR) check, wherein the HR check comprises determining whether a value of HR extrapolated from the first PPG signal sample lie between 40 and 150 cardiac cycles per minute (beats per minute).

11. The system of claim 8, wherein to model the training model during the training phase, the one or more hardware processors are further configured by the instructions to:

obtain at least one training PPG signal captured from using a training device; segment the at least one training PPG signal into a second plurality of PPG signal samples, length of each of the second plurality of PPG signal samples more than the threshold length;

perform SSC for each second PPG signal sample of the second plurality of PPG signal samples to obtain a set of clean PPG signal samples complying with the SSC and a set of noisy PPG signal samples not complying with the SSC;

create a plurality of sets of balance class subsets of the training data, each set of balanced class subset comprising the set of noisy PPG signal samples and equal number of randomly taken non overlapping clean PPG signal samples taken from the set of clean PPG signal samples;

compute a rank for each of the plurality of set of balanced class subsets based on a mRMR strengths of each of the plurality of features; and rank a mean of rank sets over every subset to obtain the set of features.

12. The system of claim 11, wherein the plurality of features comprises: SQI1 (Ratio of Cardiac diastole duration (td) to Ventricular systole duration (ts) are computed for a PPG cycle of the PPG signal sample), SQI2 (ratio of summation of every complete PPG cycle length extracted from sample to the sample length), SQI3 (mean of DTW distance of the sample), SQI4 (Variance of the ratio P1height/P2height of every cycle in a sample), SQI5 (variance of the kurtosis of every pulse), SQI6 (ratio of max PP & min PP, where PP is peak to peak distance in a sample), SQI7 (variance of amplitude ratio (amplitude of cycle/amplitude of T), SQI8 (median of direct matching (Correlation Coefficient) between cycle and T), SQI9 (variance of Pulse Width), and SQI10 (variance of root mean square error of cycle and T).

13. The system of claim 11, wherein the training device comprises an oximeter.

14. The system of claim 8, wherein the testing device comprises a smartphone.

15. A non-transitory computer-readable medium having embodied thereon a computer program for executing a method for PPG signal quality assessment, the method comprising:

obtaining a PPG signal captured using a testing device in real-time, via one or more hardware processors;

segmenting, via the one or more hardware processors, the PPG signal into a first plurality of PPG signal samples, length of each of the first plurality of PPG signal samples more than a threshold length;

performing, via the one or more hardware processors, signal sufficiency check (SSC) for each first PPG signal sample of the first plurality of PPG signal samples to obtain at least a first set of PPG signal samples complying with the SSC, the SSC performed to determine whether the first plurality of PPG signal samples comprises sufficient information for the real-time PPG signal quality assessment;

extracting a set of features from the first set of PPG signal samples, via the one or more hardware processors, the set of features representing an optimal set of features derived from a prestored training data by a training model during a training phase; and identifying, based on the set of features, each of the set of PPG signal samples as one of a noisy signal sample and a clean signal sample using a plurality of Random Forest (RF) models created during the training phase, via the one or more hardware processors.

* * * * *